(12) United States Patent
O'Neil et al.

(10) Patent No.: US 7,699,894 B2
(45) Date of Patent: Apr. 20, 2010

(54) NUCLEUS PULPOSUS TRIAL DEVICE AND TECHNIQUE

(75) Inventors: Michael O'Neil, West Barnstable, MA (US); Hassan Serhan, South Easton, MA (US); Andrew Dooris, Raynham, MA (US)

(73) Assignee: Depuy Spine, Inc., Raynham, MA (US)

( * ) Notice: Subject to any disclaimer, the term of this patent is extended or adjusted under 35 U.S.C. 154(b) by 807 days.

(21) Appl. No.: 11/315,748

(22) Filed: Dec. 22, 2005

(65) Prior Publication Data
US 2007/0162136 A1    Jul. 12, 2007

(51) Int. Cl.
*A61F 2/44* (2006.01)
(52) U.S. Cl. ................................... 623/17.12
(58) Field of Classification Search ... 623/17.11–17.16; 606/90, 92, 93, 94, 99, 86, 279; 600/7
See application file for complete search history.

(56) References Cited

U.S. PATENT DOCUMENTS

| | | | |
|---|---|---|---|
| 5,702,454 A * | 12/1997 | Baumgartner | 128/898 |
| 5,807,327 A | 9/1998 | Green | |
| 5,888,220 A | 3/1999 | Felt et al. | |
| 6,042,380 A | 3/2000 | De Rowe | |
| 6,127,597 A | 10/2000 | Beyar | |
| 6,187,048 B1 | 2/2001 | Milner | |
| 6,248,110 B1 * | 6/2001 | Reiley et al. | 606/93 |
| 6,248,131 B1 | 6/2001 | Felt | |
| 6,436,143 B1 * | 8/2002 | Ross et al. | 623/17.16 |
| 6,695,760 B1 * | 2/2004 | Winkler et al. | 600/7 |
| 6,716,216 B1 | 4/2004 | Boucher | |
| 7,004,945 B2 * | 2/2006 | Boyd et al. | 606/92 |
| 7,128,746 B2 * | 10/2006 | Singer et al. | 606/90 |
| 2003/0195628 A1 | 10/2003 | Bao | |
| 2003/0220649 A1 | 11/2003 | Bao et al. | |
| 2004/0167625 A1 | 8/2004 | Beyar | |
| 2005/0015150 A1 * | 1/2005 | Lee | 623/17.12 |
| 2005/0143827 A1 | 6/2005 | Globerman | |
| 2005/0245938 A1 * | 11/2005 | Kochan | 606/92 |
| 2005/0251005 A1 * | 11/2005 | Diwan | 600/407 |

FOREIGN PATENT DOCUMENTS

WO    WO 01/08571 A1    2/2001

OTHER PUBLICATIONS

U.S. Appl. No. 60/038,618, filed Mar. 7, 1997, Mordechai Beyar, Caesaria.
Ahrens et al., A New Procedure for Total Nucleus Removal from the Posterior Approach, European Cells and Materials, 2005, vol. 10 Suppl 3.

* cited by examiner

*Primary Examiner*—Pedro Philogene

(57) ABSTRACT

A nucleus pulposus trial device for assessing the size, shape and location of a disc space.

29 Claims, 5 Drawing Sheets

NUCLEUS PULPOSUS TRIAL DEVICE AND TECHNIQUE

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contained sulfated functional groups that retain water, thereby providing the nucleus pulposus within its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix (in particular, the MMPs (under mediation by the cytokines) begin cleaving the water-retaining portions of the proteoglycans, thereby reducing its water-retaining capabilities). This degradation leads to a less flexible nucleus pulposus, and so changes the load pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

Intervertebral disc degeneration causes a number of clinical problems, including sequelae related to reduced disc height and herniation. In many cases, a simple discectomy can effectively relieve pain, but in time results in further collapse of the disc space because the intervertebral disc can no longer resist body loads the same as a healthy disc. Spine fusion procedures represent another state of the art treatment for disc problems. Fusion generally involves the use of interbody fusion cages and spinal fixation systems to immobilize the fusion site.

In an effort to substantially maintain the patient's range of motion and to reduce tissue damage associated with surgical intervention, the art has considered nucleus pulposus replacement and enhancement devices. Many of these devices are designed to fill at least a portion of the void left by removal of the nucleus pulposus portion of the disc and provide joint flexibility and shock absorption. Some of the nucleus pulposus devices being evaluated are in situ cured (such as in situ cured polyurethane contained within an outer bladder and in situ cured protein polymers). Other devices under evaluation include relatively solid hydrogels (such as hydrogel contained within a UHMWPE pillow and hydrogel balls).

Other intervertebral motion devices include devices having an articulation interface and cushion-type devices.

Both the fusion and motion intradiscal implants require an accurate determination of the cleared disc space for the best performance, mechanical fit and material interdigitation of the device in order to minimize potential device movement and expulsion.

Each of the above-noted treatments involving an implant requires a removal of the natural nucleus pulposus from the disc space. This procedure is called a "discectomy".

The ability of a surgeon to accurately determine the position, size and shape of the cleared disc space during discectomy is currently limited by many factors, including the procedure approach, access, location and the size through the annular wall, as well as available intraoperative imaging techniques. Improper location, size or shape of the cleared disc space following discectomy can greatly impact the size, placement and securement of intervertebral devices that are ultimately placed in the disc space, as well as the biomechanical loading of the device and the physiologic response to the device. For example, improper lateral placement of a nucleus pulposus replacement device may cause migration or expulsion of this implant, leading to continued height loss and irritation of neighboring tissues (including nerve roots), thereby creating additional pain or requiring re-operation.

U.S. Pat. No. 5,888,220 ("Felt I") discloses a nucleus pulposus replacement device comprising an expandable bag into which in-situ curable polyurethane is injected. Felt further discloses that the placement of the bag can be radiographically verified with the use of a C-arm. See also U.S. Pat. No. 6,248,131, US Published Patent Application Nos. US 2003/0220649 ("Felt II") and US 2003/0195628. Felt II discloses some embodiments in which the balloon has metallic wires or other imageable means incorporated into it so that the balloon can be seen under fluoroscopy. Felt discloses that potential imageable materials include any metal, metal alloys, or ceramics that could be combined with a polymer, and that the imageable material can be in the form of wires, a mesh, or particles incorporated into the balloon or on its surface.

Felt does not disclose the use of a radiographic disc space trial balloon that is inflated to verify the size and geometry of the disc space.

SUMMARY OF THE INVENTION

It is an object of the present invention to provide an inflatable, intra-operative trial device and a method to determine, the size, location and geometry of an intradiscal space following discectomy. The invention improves the determination of implant sizing and placement, as well as implant performance, thereby leading to improved procedure safety and effectiveness.

Generally, the present invention relates to an in-situ expandable, disc space trial device.

In accordance with the present invention, a discectomy is first performed upon a patient having a degenerated disc to produce a disc space. Next, a balloon is inserted into the disc space through a hole in the annulus fibrosus, and inflated to conform to the size and shape of the cleared disc space. In order to visualize the shape of the balloon, the balloon is comprised of, or is inflated with, a radiographic material. Next, an imaging technique is used to visualize the inflated trial balloon and hence determine the size, location and geometry of the cleared disc space. This enables the surgeon to determine the suitable location and size of the implant and to verify that the site has been adequately prepared.

Therefore, in accordance with the present invention, there is provided a method for assessing a disc space, comprising the steps of:

a) performing a discectomy to create a disc space;
b) inserting a deflated balloon into the disc space;
c) expanding the deflated balloon to expand the balloon,
d) deflating the balloon,
e) removing the deflated balloon from the disc space, and
f) inserting an intervertebral implant into the disc space.

DETAILED DESCRIPTION OF THE INVENTION

For the purposes of the present invention, a "discectomy" involves the removal of at least a portion of the nucleus pulposus of a degenerated disc. Often, the entire nucleus pulposus is removed. Frequently, a small portion of the annulus fibrosus portion of the intervertebral disc is removed as well, thereby leaving a central disc space surrounded by the remaining portion of the annulus fibrosus.

In performing a preferred method of the present invention, first, a discectomy is performed by creating a hole in the annulus fibrosus of a degenerating disc, inserting a tissue removal instrument (such as rongeurs) into the hole, and removing nucleus pulposus tissue from the disc.

Next, a trial balloon is inserted directly into the disc cavity, preferably by being delivered through a minimally invasive cannula.

Next, the trial balloon is then inflated to conform to the cleared disc space cavity.

Next, the volume of the intradiscal cavity is obtained by monitoring either the volume of material injected into the balloon, or the pressure in comparison to known balloon expansion values. Intra-operative imaging is then performed to determine the coronal, saggital, and axial placement of the device, as well as the size, angle and geometry of the cleared disc space. The intra-operative imaging may include the use of a C-arm, cineradiography or image guided surgery.

Next, the surgeon makes an intraoperative determination as to whether an adequate intradiscal cavity has been created. If the surgeon determines that the intradiscal cavity is insufficient (for example, the disc space is located to the left of center), the surgeon deflates and removes the trial balloon, performs additional discectomy, and then again ascertains the disc space clearance with the trial balloon.

Based upon the surgeon's assessment of the amount, size and shape of the disc space cleared, the surgeon can select the appropriate disc treatment procedure, including the injection or insertion of nuclear and annular augmentation materials, disc replacement devices or fusion devices. For example, if excessive degenerative or surgical endplate damage is apparent by assessment with the trial balloon, the surgeon may decide that the selection of an injectable fusion cage will improve the patient outcome when compared to replacement of the nucleus with a material that allows motion at the functional spinal unit.

Therefore, in preferred embodiments, there is provided a method for assessing a disc space, comprising the steps of:

a) performing a discectomy to create a disc space;
b) inserting a deflated balloon into the disc space;
c) expanding the deflated balloon to expand the balloon,
d) deflating the balloon,
e) removing the deflated balloon from the disc space, and
f) inserting an intervertebral implant into the disc space.

The above steps will now be discussed in greater detail.

Figure 1A:
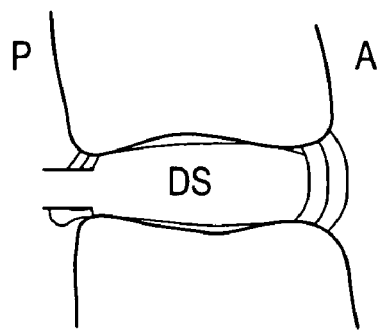
FIGS. 1a-1c represent saggital, frontal and top views of an intervertebral disc after a conventional discectomy.
Figure 1B:
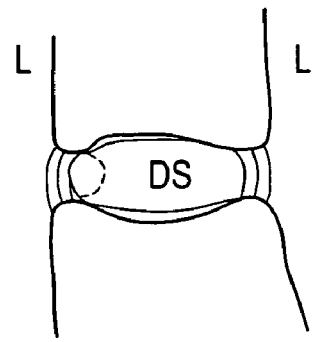
Figure 1C:
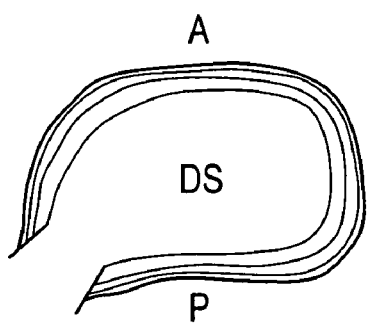

Now referring to FIGS. 1a-c, in a preferred embodiment of the present invention, at least a portion of each of the nucleus pulposus and the annulus fibrosus is removed with a disc removal instrument to create a disc space DS. Suitable disc removal instruments include rongeurs, trephines, burrs and curettes. In some embodiments, the method includes removing at least a portion of the nucleus pulposus, wherein the removal step includes creating a vacuum or providing irrigation. In some embodiments, the irrigation is provided by the same cannulated instrument that delivers and expands the balloon. In some embodiments, the method includes removing at least a portion of the nucleus pulposus, wherein the removal step is achieved via chemical dissolution of the nucleus pulposus.

Figure 2A:
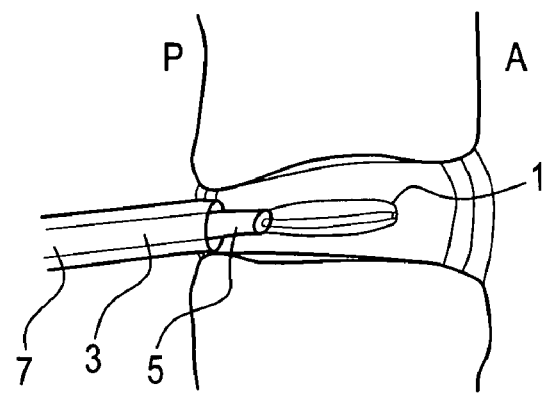
FIGS. 2a-2c represent saggital, frontal and top views of the insertion of a balloon of the present invention into an intervertebral disc space.
Figure 2B:
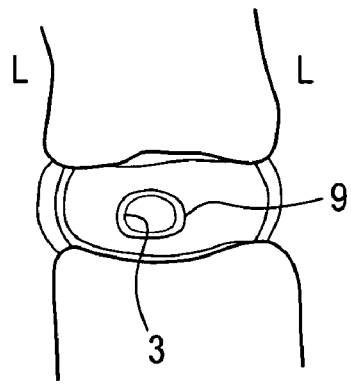
Figure 2C:
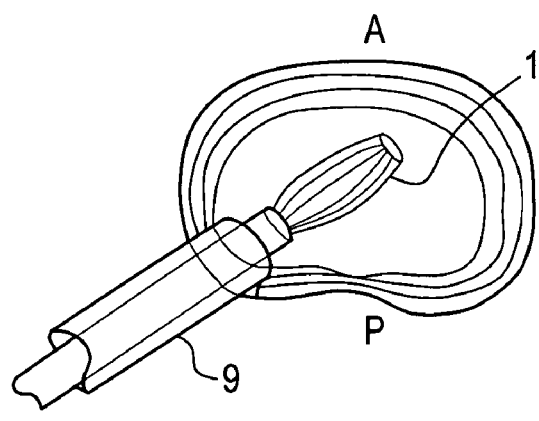

Now referring to FIGS. 2a-c, the trial balloon is inserted into the disc space in a deflated form. The trial device comprises:

a) a balloon 1 having a lumen and comprising an expandable material, and
b) a tube 3 having a proximal end portion 7, a distal end portion 5, and a throughbore (not shown)

wherein the balloon lumen is connected to the distal end portion of the tube and is in fluid communication with the throughbore.

In some embodiments, and as shown, the trial balloon is inserted into the disc space through a cannula 9. In others, it is inserted without the aid of a cannula.

The balloon can be delivered to the disc space by any suitable means, e.g., in deflated form retained within or upon the end of a rigid or semi-rigid rod or tube.

In some embodiments, the balloon may also be inserted through a hole created in an endplate of an adjacent vertebra above or below the target disc. The balloon may be inserted into the disc space via a posterior, anterior or anterolateral approach.

Once positioned within the disc space, either centrally within the annular shell or at the edge of the annular rim, a suitable gas (e.g., nitrogen or carbon dioxide), liquid or other flowable expansion medium can be delivered through the tube in order to inflate the balloon in situ in a substantially radial, axial and/or longitudinal direction. In some embodiments, beads or other solid media are selected to be the expansion medium and are simply packed into the balloon through the tube.

Figure 3A:
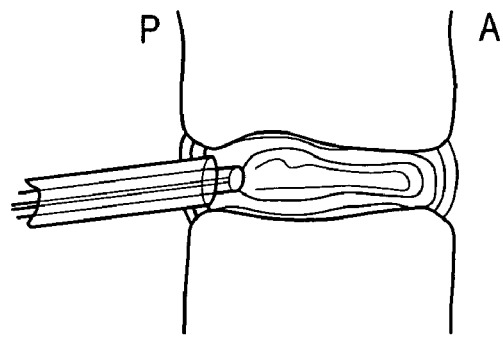
FIGS. 3a-3c represent saggital, frontal and top views of the inflation of a balloon of the present invention within an intervertebral disc space.
Figure 3B:
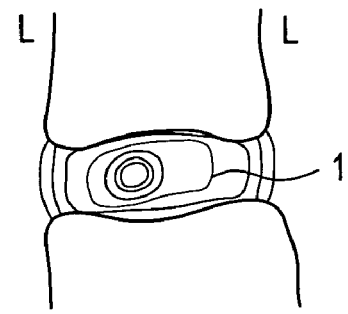
Figure 3C:
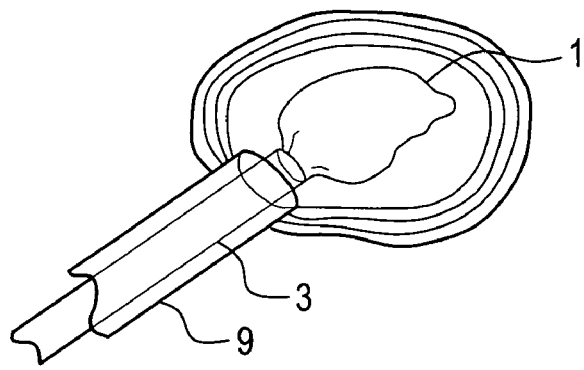

Now referring to FIGS. 3a-c, the trial balloon is expanded while in the disc space. Preferably, the trial balloon is expanded with radio-opaque media (not shown), such as a radio-opaque gas or liquid, or with radio-opaque beads. Once expanded, the balloon may be imaged intra-operatively in order to determine the size, shape and location of the disc space. In FIGS. 3a-3c, the balloon is shown as only partially expanded in the disc space. Preferably, the balloon is expanded to completely fill the disc space.

The balloon has at least one lumen, an inside surface, and an outer surface. Also, the expandable balloon has an upper side, a lower side, an anterior side and a posterior side. The balloon is typically expanded by passing an expansion medium, such as a fluid or beads, through the lumen to fill the balloon.

Suitable materials for preparing balloons of the present invention may include those that are presently used for such purposes as balloon angioplasty. Suitable materials provide an optimal combination of such properties as compliance, biostability and biocompatability, and mechanical characteristics such as elasticity and strength. Balloons can be provided in any suitable form, including those having a plurality of layers and those having a plurality of compartments when expanded. A useful trial device will include the balloon itself, together with a delivery catheter (optionally having a plurality of lumens extending longitudinally therewith), and fluid or gas pressure means.

The balloon is typically made of an expandable material such as a plastic or elastomeric material. Examples thereof include silicone, polyurethane, polyethylene terephthalate, polycarbonate, thermoplastic elastomers and copolymers such as ether-ketone polymers such as poly(etheretherketone). Such polymeric materials can be used in either unsupported form, or in supported form, e.g., by the integration of fibers therein. In addition, the balloon may be made out of any of a wide variety of woven or nonwoven fibers, fabrics, metal mesh such as woven or braided wires, and carbon. Biocompatible fabrics or sheet material such as ePTFE and Dacron™ may also be used.

In a particularly preferred embodiment, the balloon comprises a material selected from the group consisting of polyolefin copolymers, polyethylene, polycarbonate, polyethylene terephthalate, ether-ketone polymers, woven fibers, nonwoven fibers, fabrics and metal mesh.

A radio-opaque material may be mixed with the expandable material to provide a radio-opaque balloon having imaging capability. The radio-opaque material may be provided in the form of a filler, particles, wires or shapes. Suitable radio-opaque materials include barium, barium sulfate, calcium or metallic materials.

The balloon can include markers commonly used in image guided surgery to allow three dimensional reconstruction of the cleared disc space as compared to a preoperatively obtained reconstructed MRI and/or CT. The markers are preferably located upon the outside surface of the balloon. The markers may have spatially varying sizes, shapes or concentrations.

In some embodiments, the expandable material of the balloon can be a non-compliant material that expands to a predetermined size. In some preferred embodiments, the distraction of the disc space is accomplished by the inflatable, rigid (non-compliant) balloon. The non-compliant balloon can be delivered in deflated form to the interior of the annulus and there inflated in order to distract the disc space and provide a region for the delivery of the intervertebral implant. The balloon is preferably of sufficient strength and of suitable dimensions to distract the space to a desired extent and to maintain the space in distracted position for a sufficient period of time.

In some embodiments, the balloon includes features that limit expansion in certain planes. For example, in one embodiment, the balloon has a bellows shape that has a predetermined footprint and allows only vertical expansion.

In other embodiments, the expandable material of the balloon can be a compliant material that allows conformance with cleared intradiscal cavities and sub-cavities of random shape.

The balloon may be comprised of single or multiple chambers or lobes, which optionally have continuous cavities between them. The device may include multiple balloons, thereby providing an opportunity to evaluate, ascertain and address cases which may have a bias towards the anterior-posterior or left-right lateral sides. Multiple chamber balloons are also helpful for assessing the degree of tightness in different regions of the disc; for loosening ligamentous structures surrounding the disc space, and for correcting alignment of the disc space.

In one embodiments, the balloon has a wedged shape so that the height of the anterior portion of the expanded device is greater than the height of the posterior portion of the expanded device. This allows the surgeon to restore lordosis when the intervertebral implant is used in either the lumbar or cervical regions of the spine. Preferably, the wedged shape produces an angle of between 5 and 20 degrees, more preferably between 5 and 15 degrees.

In preferred embodiments, the height of the medial portion of the balloon is greater than the height of either lateral portion of the expanded device. This geometry more closely mimics the natural doming of the disc space.

In some embodiments, the device can comprise a balloon of semicircular, circular, cylindrical, bilateral (comprising more than one balloon), or a generally crescent (or banana-like) shape.

In some embodiments, the inflatable device of this embodiment has a configuration designed to match the geometry of the disc space, and is selected from the group consisting of an anterior lumbar interbody fusion (ALIF) configuration, a posterior lumbar interbody fusion (PLIF) configuration, a motion device configuration, and an anterior cervical discectomy and fusion (ACDF) configuration.

Upon inflation, the balloon can have a footprint that substantially corresponds to a rim of a vertebral endplate, wherein the anterior area height is greater than said posterior area height. More preferably, upon expansion, at least a portion of the balloon has a generally cylindrical shape thereby defining an axial dimension and a radial dimension.

In some preferred embodiments, the balloon may also be used to distract the cleared disc space. When inflated, a non-compliant balloon may provide rigid walls (e.g., when they are fiber-supported or bellows -supported) that are sufficiently strong to distract the space. An inflatable device providing sufficient strength and dimensions for distraction can be prepared using conventional materials. In one embodiment, the uninflated balloon can be delivered to the center of the annular shell, and there inflated to expand the annular shell and in turn, distract the space. Preferably, the expansion medium is injected in an amount sufficient to distract the space.

As used herein the word "distraction" will refer to the separation of the intervertebral joint surfaces to a desired extent, without rupture of their binding ligaments and without displacement. Distraction can be accomplished by any suitable means including, for example, hydrostatic means. In one embodiment, the trial balloon is used as a distraction device. By the use of distraction, the disc space can be sufficiently re-established to achieve any desired final dimensions and position. Optionally, and preferably, the means used to accomplish distraction also serves the purpose of forming one or more barriers (e.g., balloons) for the flowable expansion media. If distraction is desired, then the disc space can be distracted prior to and/or during either a discectomy itself and/or delivery of a flowable expansion medium.

A constricted disc space is generally on the order of 3 to 4 mm in height. Suitable distraction means are capable of providing on the order of about 3 atmospheres to about 4 atmospheres, (or on the order of about 40 psi to about 60 psi) in order to distract that disc space to on the order of 8 to 12 mm in height. Preferably, when used for distraction, the balloon of the present invention is designed to withstand at least 1 MPa of pressure, more preferably at least 2 MPa, more preferably at least 3 MPa.

Distraction may occur via a multitude of steps or iterations, thereby allowing the soft tissue to relax, thus reducing the risk of soft tissue damage.

In some embodiments, the balloon is injected with an expansion medium, such as a gas or liquid, or a solid particulate material. This injected material expands the balloon to conform to the intradiscal cavity and may, if radio-opaque, also enhance imaging capabilities. Suitable radio-opaque expansion media include barium, barium sulfate, calcium or metallic media.

Therefore, also in accordance with the present invention, there is provided a nucleus pulposus trial device for assessing a disc space, comprising:

a) a balloon comprising an expandable material and having a lumen, b) a tube having a proximal end portion, a distal end portion, and a throughbore, and c) a radio-opaque expansion medium contained within the lumen wherein the balloon is connected to the distal end portion of the tube and is in fluid connection with the throughbore.

Preferably, the expansion media of the in situ formed device can be delivered percutaneously (e.g., through a cannula having a diameter of no more than 6 mm, preferably no more than 2 mm). However, the expansion media of the in-situ formed device can also be delivered in cannulae of much larger dimension (such as up to 18 mm, or through a Craig needle). More preferably, the expansion media of the in-situ formed device are delivered into the disc space in the form of an injectable fluid.

The flowable expansion medium can be delivered, as with a pump, from a storage canister to the delivery cannula on demand.

In terms of its component parts, in one preferred balloon delivery system of the present invention, there is provided an inflatable device, a motor drive unit, with a remote controller, associated tube sets, a nonscope inflow delivery cannula having independent fluid dynamics pressure and flow rate adjustments, and attachments for the flush, vacuum, waste canister, and overflow jars.

It has been reported in the literature that balloons inserted into the disc space may be subject to retropulsion. Therefore, in some embodiments of the present invention, and particularly those that include distraction, upon expansion, the inflatable device forms an upper surface having a first plurality of teeth projecting outwards from the upper surface. Upon expansion of the device, these teeth will project in the direction of the upper endplate and, upon complete expansion of the device, will engage the endplate to from a secure interlock with the endplate and resist retropulsion.

Preferably, the teeth are made of a stiff non-resorbable material, such as polyetheretherketone (PEEK). Preferably, the teeth have a height of between 0.5 mm and 1.5 mm, and have a triangular cross-section.

In some embodiments of the present invention, upon expansion, the inflatable device forms an upper surface formed of a material having a high coefficient of friction. Upon expansion of the device, the high coefficient of friction of the upper and lower surfaces will case a drag upon any movement of the upper surface and therefore keep the device in place and resist retropulsion.

Preferably, the high friction upper and lower surfaces of the inflatable device are made from a material selected from a group consisting of polyether block copolymer (PEBAX), ABS (acrylonitrile butadiene styrene); ANS (acrylonitrile styrene); Delrin®; PVC (polyvinyl chloride); PEN (polyethylene napthalate); PBT (polybutylene terephthalate); polycarbonate; PEI (polyetherimide); PES (polyether sulfone); PET (polyethylene terephthalate); PETG (polyethylene terephthalate glycol), high and medium melt temperature: polyamides, aromatic polyamides, polyethers, polyesters, Hytrell®, polymethylmethacrylate, polyurethanes: copolymers, EVA (ethylene vinyl acetate) or ethylene vinyl alcohol; low, linear low, medium and high density polyethylenes, latex rubbers, FEP, TFE, PFA, polypropylenes, polyolefins; polysiloxanes, liquid crystal polymers, inomers, Surlins, silicone rubbers, SAN (styrene acrylonitrile), nylons: 6, 6/6, 6/66, 6/9, 6/10, 6/12, 11, all PEBAXs 12; polyether block amides; and thermoplastic elastomers.

Balloons of the present invention can be made using materials and manufacturing techniques used for balloon angioplasty devices. U.S. Pat. No. 5,807,327 ("Green") discloses balloons that may be used in the present invention. The materials disclosed by Green for the formation of the balloon include tough non-compliant layer materials (col. 8, lines 18-36 of Green) and high coefficient of friction layer materials (col. 8, lines 42-54 of Green).

Generally, the balloon is deliverable through a cannula having an inside diameter of between 3 mm and 18 mm, preferably between 4 mm and 12 mm, more preferably between 5 mm and 10 mm.

In some preferred embodiments, a cannula having an inner diameter of no more than 6 mm, is inserted into the disc space.

In some embodiments in which the surgeon desires to minimize the size of the incision, the balloon is preferably deliverable through a cannula having an inside diameter of between 0.5 mm and 6 mm, preferably between 1 mm and 4 mm, more preferably between 2 mm and 3 mm.

Figure 4A:
FIGS. 4a-4b represent a device of the present invention having a collapsed balloon having pleats and folds.
Figure 4B:
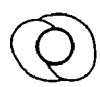

Now referring to FIGS. 4a-b, the deflated balloon may be provided in a twisted or helical shape 11. This twisted or helical shape allows for easier insertion of the deflated balloon into the cleared disc space.

Figure 5A:
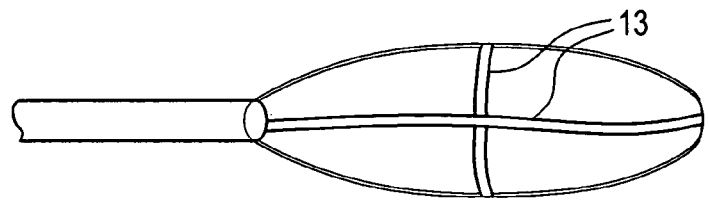
FIGS. 5a-5b represent a balloon of the present invention provided with constraints such as wire bands or mesh.
Figure 5B:
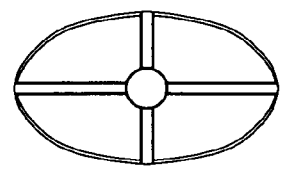

Now referring to FIGS. 5a-b, the balloon may be provided with constraints such as wire bands or mesh 13. These constraints limit the motion or expansion of the balloon in various planes. These constraints may also be radio-opaque.

Figure 6A:
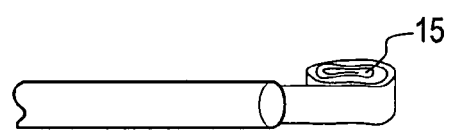
FIGS. 6a-6b represent a balloon of the present invention provided in a coiled shape.
Figure 6B:

Now referring to FIGS. 6a-b, the balloon may be provided in a coiled shape 15. The coil allows for motion or expansion of the balloon in a horizontal plane and minimizes vertical expansion of the balloon.

Figure 7A:
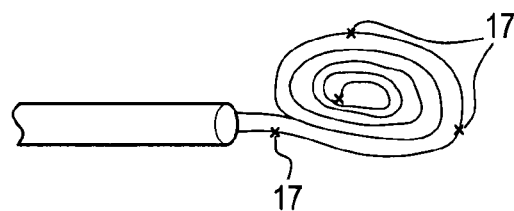
FIGS. 7a-7b represent the balloon of FIG. 6 is provided with radio-opaque markers.
Figure 7B:
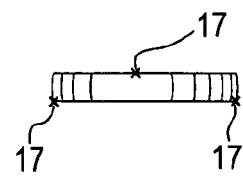

Now referring to FIGS. 7a-b, the balloon of the trial device is provided with radio-opaque markers 17.

Figure 8A:
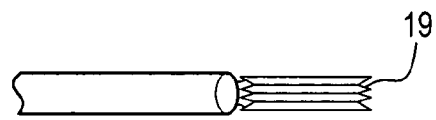
FIGS. 8a-8c represent a balloon of the present invention provided in a bellows shape.
Figure 8B:
Figure 8C:
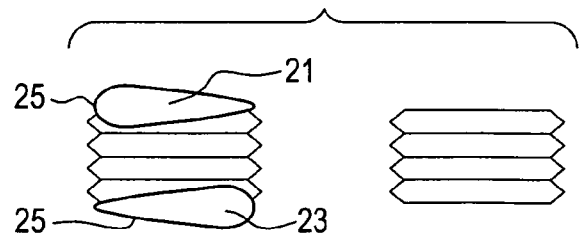

Now referring to FIGS. 8a-c, the balloon may be provided with a plurality of pleats 19 to produce a bellows shape. The bellows shape constrains motion and expansion of the balloon to the vertical direction. The top 21 and bottom 23 of the bellows balloon can comprise radio-opaque markers 25.

Therefore, also in accordance with the present invention, there is provided a nucleus pulposus trial device for assessing or restoring a disc space, comprising:
 a) a balloon comprising an expandable material and having a lumen and a bellows shape, wherein the bellows shape comprises a non-compliant bottom portion, an expandable intermediate portion, and a non-compliant upper portion, and
 b) a tube having a proximal end portion, a distal end portion and a throughbore, wherein the balloon is connected to the distal end portion of the tube and is in fluid connection with the throughbore.

In some embodiments, the balloon comprises a plurality of lobes or chambers. These chambers can be constructed in such a way that they can be filled consecutively or simultaneously. The use of multiple chambers can allow an increased force or filling in specified planes or directions.

Figure 9:
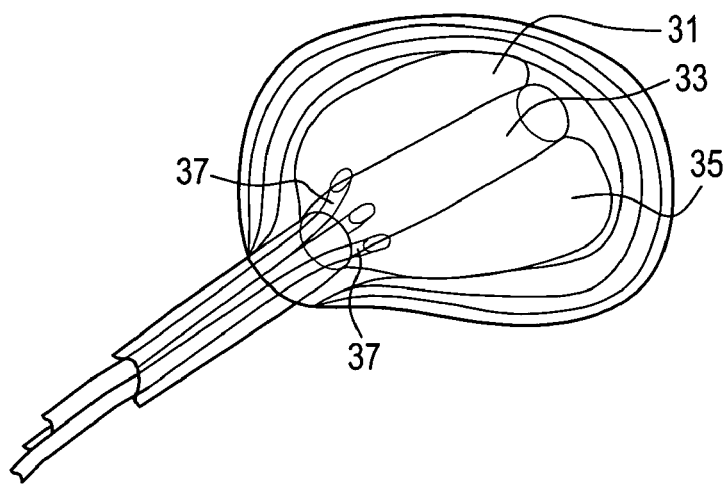
FIG. 9 represents a balloon of the present invention having a plurality of lobes or chambers.

Now referring to FIG. 9, there is provided a multi-chamber balloon having an anterior chamber 31, a central chamber 33 and a posterior-lateral chamber 35, wherein each chamber is separately filled by a different tube 37.

Figure 10A:
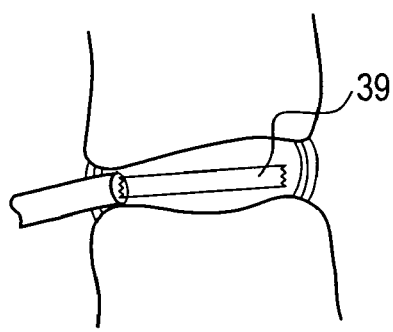
FIGS. 10a-10c represent a trial device having a bellows shape for assessing a disc space prior to a fusion.
Figure 10B:
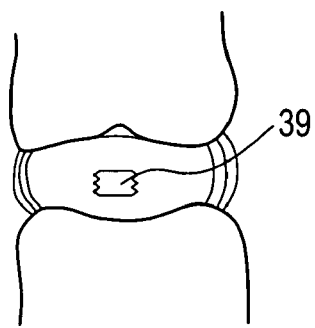
Figure 10C:
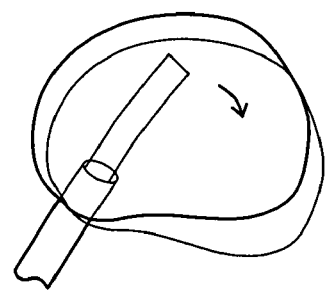

FIGS. 10a-10c represent a trial device having a bellows shape for assessing a disc space. This type of device may be particularly suited for use prior to a fusion. In some embodiments, the device may be rotated (as in FIG. 10c) after insertion.

Figure 11A:
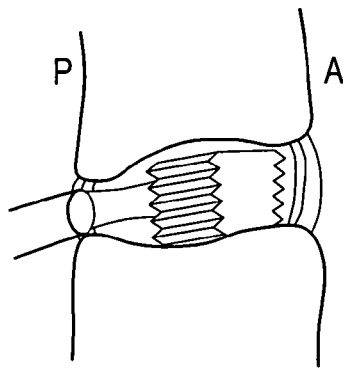
FIGS. 11a-11c represents a bellows-type trial device having a crescent shape.
Figure 11B:
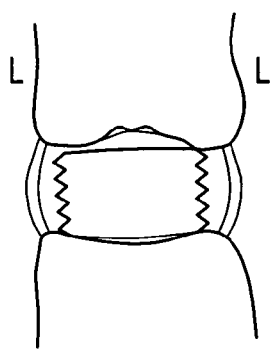
Figure 11C:
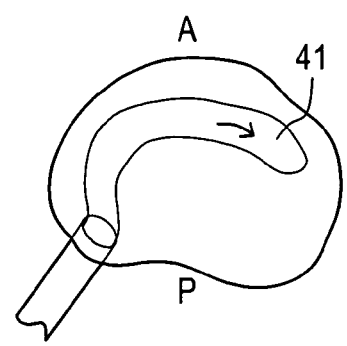

Now referring to FIGS. 11a-c, the balloon may be provided as a bellows in a banana or crescent shape 41. The bellows configuration constrains motion and expansion of the balloon to the vertical direction, while the banana shape provides a template for a banana-shaped fusion device.

Figure 12A:
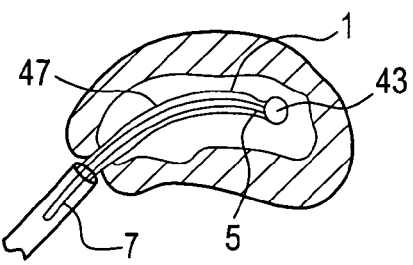
FIGS. 12a-12b represent a device of the present invention having a distally located radio-opaque probe have a blunted end (such as a ball) that can be used to maneuver the device into the disc space prior to expansion of the balloon.
Figure 12B:
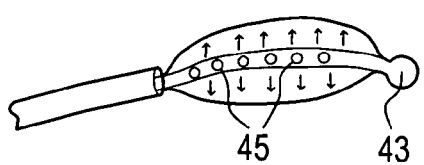

Now referring to FIGS. 12a-b, in some embodiments, the device includes a distally located radio-opaque probe having a blunted end 43 (such as a ball) that can be used to maneuver the device into the disc space prior to expansion of the balloon. This device might be useful for very narrow disc spaces in which the balloon may not be able to open, even after the disc material has been removed.

Therefore, also in accordance with the present invention, there is provided a nucleus pulposus trial device for assessing a disc space, comprising:
 a) a balloon 1 comprising an expandable material and having a lumen, and
 b) a tube having a proximal end portion 7, a distal end portion 5, an outer surface 47, a throughbore, a plurality of holes 45 extending from the outer surface of the distal end portion of the tube to the throughbore and a closed distal end 43, wherein the lumen of the balloon is connected to the distal end portion of the tube and is in fluid connection with the throughbore.

Figure 13A:
FIGS. 13a-13b represent a device of the present invention having protrusions that can protrude into irregularly shaped disc cavities.
Figure 13B:
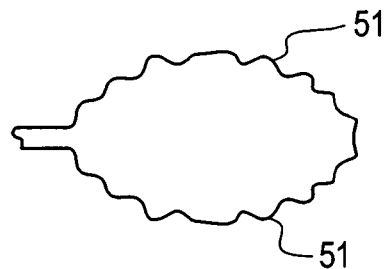

Now referring to FIGS. 13a-b, in some embodiments, the device has protrusions that can protrude into irregularly shaped disc cavities. FIG. 13a shows the device in a collapsed form, while FIG. 13b shows the device in an expanded form.

Figure 14A:
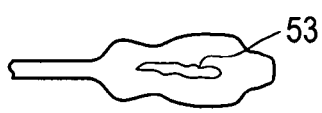
FIGS. 14a-14b represents a donut-shaped trial having a central hole.
Figure 14B:
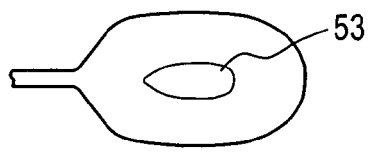

Now referring to FIGS. 14a-b, in some embodiments, the balloon is donut-shaped with non-uniform stiffness biasing expansion outward which may also encourage the filling of irregularly shaped disc spaces. The center 53 of this space may be open or filled with a rubbery or otherwise deformable material.

EXAMPLE

In performing a preferred prophetic method of the present invention, the patient is brought to the pre-surgical area and prepped. Anesthesia is then induced and the area of the spine is further prepped. A small incision through the muscles is opened under dissecting microscopic visualization. The incision is made as small as possible and is longitudinal in the plane of the spine. The paravertebral muscles are separated by blunt dissection and held apart with forceps and dividers. The intervertebral disc area is visualized, with initial exposure down to the lamina. The area below the lamina, at the point of the intervertebral foramina, can also be exposed.

The disc is examined for extruded material and any extruded material is removed. Magnetic resonance imaging ("MRI") data can be used to determine the integrity of the annulus fibrosis at this point. An arthroscope is inserted into the disc and used to examine the inside of the annulus. Optionally, an intraoperative discogram can be performed, in which a dye material is inserted and visualized in order to substantiate the integrity of the annulus fibrosis. Points of weakness, or rents, in the annulus fibrosis are identified and located and suitable means, e.g., a bioabsorbable glue is employed to block these rents.

Next, a deflated balloon is inserted into the disc space and a radio-opaque expansion fluid is delivered into the balloon lumen, thus expanding the balloon. The surgeon then turns on the X-ray and assesses the size, shape and location of the disc space through visualization of the radio-opaque expansion medium. Upon confirming the appropriateness of the disc space, the surgeon deflates and withdraws the trial balloon and proceeds to insert an intervertebral implant into the disc space based upon the determined size, shape and location.

We claim:

1. A nucleus pulposus trial device for assessing a disc space, comprising:
 a) a balloon comprising an expandable material and having a lumen, and
 b) a tube having a proximal end portion, a distal end portion, an outer surface, a throughbore, a plurality of holes extending from the outer surface of the distal end portion of the tube to the throughbore and a closed distal end,
 wherein the lumen of the balloon is connected to the distal end portion of the tube and is in fluid connection with the throughbore,
 wherein the balloon further comprises a radio-opaque material mixed with the expandable material.

2. The device of claim 1 wherein the expandable material is selected from the group consisting of silicone, polyurethane, polycarbonate, polyethylene terephthalate, thermoplastic elastomers and copolymers.

3. The device of claim 1 wherein the closed distal end of the tube is rounded.

4. The device of claim 1 wherein the balloon further comprises an outer surface, and wherein the device further comprises radio-opaque markers on the surface of the balloon.

5. A nucleus pulposus trial device for assessing a disc space, comprising:
   a) a balloon comprising an expandable material and having a lumen,
   b) a tube having a proximal end portion, a distal end portion, and a throughbore, and
   c) a radio-opaque expansion medium consisting essentially of radio-opaque beads contained within the lumen,
   wherein the balloon is connected to the distal end portion of the tube and is in fluid connection with the throughbore.

6. The device of claim 5 wherein the expandable material is selected from the group consisting of silicone, polyurethane, polycarbonate, polyethylene terephthalate, thermoplastic elastomers and copolymers.

7. The device of claim 5 wherein the balloon is substantially non-compliant.

8. The device of claim 5 wherein the balloon is substantially compliant.

9. The device of claim 5 wherein the balloon comprises a feature for limiting expansion.

10. The device of claim 5 wherein the balloon has a bellows shape.

11. The device of claim 5 wherein the balloon has a plurality of chambers.

12. The device of claim 5 wherein the balloon has a twisted shape in a deflated condition.

13. The device of claim 5 wherein the balloon has a coiled shape.

14. The device of claim 5 wherein the balloon has a crescent shape.

15. A method for assessing a disc space, comprising the steps of:
   a) performing a discectomy to create a disc space;
   b) inserting a deflated balloon into the disc space;
   c) expanding the deflated balloon with radio-opaque media to expand the balloon,
   d) deflating the balloon,
   e) removing the deflated balloon from the disc space, and
   f) inserting an intervertebral implant into the disc space.

16. The method of claim 15 wherein the step of expanding the trial balloon includes inflating the trial balloon.

17. The method of claim 15 wherein the radio-opaque media is a radio-opaque gas or liquid.

18. The method of claim 15 wherein the radio-opaque media is a plurality of radio-opaque beads.

19. The method of claim 15 wherein the balloon comprising a radio-opaque material.

20. The method of claim 15 wherein the discectomy is performed with a vacuum.

21. The method of claim 15 wherein the discectomy is performed with irrigation.

22. The method of claim 15 wherein the discectomy is performed with a chemical that degrades a nucleus pulposus.

23. The method of claim 15 further comprising a step of assessing a shape of the expanded balloon with an imaging technique.

24. The method of claim 15 further comprising a step of assessing a location of the expanded balloon with an imaging technique.

25. The method of claim 15 further comprising a step of assessing a volume of the expanded balloon.

26. The method of claim 15 wherein the step of expanding the balloon distracts the disc space.

27. The method of claim 15 wherein the step of expanding the balloon corrects alignment of the disc space.

28. The method of claim 15 wherein the step of expanding the balloon provide lordosis to the disc space.

29. The method of claim 15 wherein the step of expanding the balloon loosens ligamentous structures surrounding the disc space.

* * * * *